(12) United States Patent
Durtschi et al.

(10) Patent No.: US 8,253,577 B2
(45) Date of Patent: *Aug. 28, 2012

(54) WIRELESS MEDICAL GASES MANAGEMENT SYSTEM

(75) Inventors: Franck-Stephane Durtschi, Bear, DE (US); Olivier J. Cadet, Bear, DE (US)

(73) Assignee: American Air Liquide, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/951,327

(22) Filed: Nov. 22, 2010

(65) Prior Publication Data

US 2011/0061648 A1    Mar. 17, 2011

Related U.S. Application Data

(63) Continuation of application No. 11/735,862, filed on Apr. 16, 2007, now Pat. No. 7,920,067.

(51) Int. Cl.
*G08B 21/00* (2006.01)
(52) U.S. Cl. .................. 340/605; 340/539.12
(58) Field of Classification Search .......... 340/605, 340/539.12, 604; 702/45
See application file for complete search history.

(56) References Cited

U.S. PATENT DOCUMENTS

| | | | | |
|---|---|---|---|---|
| 4,155,357 | A | * | 5/1979 | Dahl ................ 128/202.22 |
| 4,302,640 | A | * | 11/1981 | Vicenzi et al. ......... 200/81 R |
| 5,953,682 | A | * | 9/1999 | McCarrick et al. ........ 702/45 |
| 6,474,334 | B1 | | 11/2002 | Lemer |
| 7,089,932 | B2 | * | 8/2006 | Dodds ................ 128/202.22 |

FOREIGN PATENT DOCUMENTS

| | | |
|---|---|---|
| FR | 2708713 | 2/1995 |
| GB | 2201098 | 8/1988 |

OTHER PUBLICATIONS

Innovative Wireless Technologies; The Wireless Meter Reader; http://www.wtwireless.com/MeterReader.htm; printed from Internet Jul. 23, 2007; 5 pgs.
INOTherapeutics; 2004; INOVent Delivery System; http://www.inotherapeutics.com/products_overview.htm; printed from Internet Jul. 23, 2007; 4 pgs.
Praxair; 2007; Medical Gas Systems Testing and Servicing; http://www.praxair.com/praxair.nsf/1928438066cae92d85256a63004b880d/2b915c776ca8c19b85256b8900736867?OpenDocument; printed from Internet Jul. 23, 2007; 2 pgs.
Air Products and Chemicals, Inc.; 2004; Medical Gases and Support Services Brochure; http://www.airproducts.com/nr/rdonlyres/f677742d-f561-4e79-87e0-7f459ac51c52/0/na_medical8pgbrochure4.pdf; printed from Internet Jul. 23, 2007; 8 pgs.
Air Liquide Sante; TAEMA web site; http://www.taema.fr/en/accueil.htm#hopital; printed from Internet Jul. 23, 2007; 2 pgs.
Search Report for EP 08152324.

* cited by examiner

*Primary Examiner* — Jeffery Hofsess
(74) *Attorney, Agent, or Firm* — Elwood L. Haynes

(57) ABSTRACT

The present invention generally provides methods and systems for managing a medical gas system by using wireless sensors located at the point of use. In one embodiment, a wireless sensor is fixed to a gas outlet, and is configured to measure gas flow, and to detect whether the gas outlet is connected to a medical device. The gas flow and connection data is included in a wireless signal that is transmitted to a remote server. The data received by the server may be analyzed to determine if any local or system leaks are occurring. In addition, the data may be used to monitor patient therapies, to calculate costs, and to determine replenishment points.

8 Claims, 5 Drawing Sheets

WIRELESS MEDICAL GASES MANAGEMENT SYSTEM

CROSS-REFERENCE TO RELATED APPLICATIONS

This application is a Continuation of U.S. Non-Provisional application Ser. No. 11/735,862, filed Apr. 16, 2007 now U.S. Pat. No. 7,920,067 which is herein incorporated by reference.

BACKGROUND

In modern medical facilities such as hospitals, there is typically a need to supply medical gases to various points of use, for example patient rooms, operating rooms, examination rooms, and the like. Commonly, the medical gases are centrally stored, and then distributed to various points of use by a network of gas conduits. Typically, the supply of gases in such facilities is monitored by measuring the gas pressure (or liquid level, for gases stored in liquid form) at the storage container (e.g., pressure cylinder or tank). When the available amount falls below a predefined minimum level, additional quantities are ordered to replenish the gas supplies.

However, this approach is only suitable for managing the global (i.e., system-wide) usage of medical gases, and does not provide measurements of gas consumption at specific points of use. Conventionally, the localized management of medical gases is performed by manually setting flow rates at each point of use, and then manually collecting the flow rate data. However, these manual approaches are tedious and time-consuming.

Additionally, such conventional approaches do not provide the ability to detect and isolate gas leaks. Leaks can occur for various reasons, such as equipment not being connected properly, valves being left open, cracks in pipes, etc.

Therefore, there is a need for improved techniques for the management of medical gases.

SUMMARY

One embodiment of the invention provides a method for monitoring the use of medical gases, comprising: receiving, from a flow sensor fixed to a medical gas conduit, a wireless signal indicating the presence of a flow of gas through the conduit, wherein the conduit carries gas to a gas outlet; determining whether a medical device is properly connected to the outlet; and if not, generating an alert communicating the existence of a potential leak at the gas outlet.

Another embodiment of the invention provides a method for monitoring the use of medical gases, comprising: receiving a plurality of wireless signals, each coming from one of a plurality of flow sensors, wherein each flow sensor is configured to measure the flow rate of gas through one of a plurality of gas outlets, wherein the gas flowing to the plurality of gas outlets is supplied by a gas delivery system fluidly coupled to at least one gas source; determining, based on the plurality of wireless signals, the total amount of gas used at the plurality of gas outlets; determining, based on one or more measurements of the at least one gas source, the amount of gas that has been removed from the at least one gas source; determining whether the total amount of gas used at the plurality of gas outlets differs, by a predetermined margin, from the amount of gas that has been removed from the at least one gas source; and if so, generating an alert communicating the existence of a potential leak in the gas delivery system.

Yet another embodiment of the invention provides a computer-readable storage medium storing instructions which when executed by a processor, performs a method, comprising: receiving, from a flow sensor fixed to a medical gas conduit, a wireless signal indicating the presence of a flow of gas through the conduit, wherein the conduit carries gas to a gas outlet; determining whether a medical device is properly connected to the outlet; and if not, generating an alert communicating the existence of a potential leak at the gas outlet.

Yet another embodiment of the invention provides a computer-readable storage medium storing instructions which when executed by a processor, performs a method, comprising: receiving a plurality of wireless signals, each coming from one of a plurality of flow sensors, wherein each flow sensor is configured to measure the flow rate of gas through one of a plurality of gas outlets, wherein the gas flowing to the plurality of gas outlets is supplied by a gas delivery system fluidly coupled to at least one gas source; determining, based on the plurality of wireless signals, the total amount of gas used at the plurality of gas outlets; determining, based on one or more measurements of the at least one gas source, the amount of gas that has been removed from the at least one gas source; determining whether the total amount of gas used at the plurality of gas outlets differs, by a predetermined margin, from the amount of gas that has been removed from the at least one gas source; and if so, generating an alert communicating the existence of a potential leak in the gas delivery system.

Yet another embodiment of the invention provides a system, comprising: a medical facility, comprising: a plurality of locations configured for patient care, each comprising at least one gas fixture, wherein each gas fixture is configured to connect to and supply medical gases to at least one medical device; at least one medical gas source; at least one wireless receiver; a plurality of gas conduits, configured to distribute medical gases from the at least one gas source to each of the gas fixtures. In addition, the system further comprises a plurality of wireless sensors disposed on the plurality of gas fixtures, each comprising: a flow sensor configured to measure a flow of gas through the gas fixture on which it is disposed, a connection sensor configured to determine whether a medical device is properly connected to the gas fixture on which it is disposed, and a wireless transmitter configured to transmit a wireless signal to the at least one wireless receiver, wherein the wireless signal includes data indicating whether a flow of gas is detected and whether a medical device is properly connected. In addition, the system further comprises a gas management application, configured to receive the data included in the wireless transmissions, and to selectively generate alerts communicating the existence of a potential leaks at the gas fixtures based on the received data.

Yet another embodiment of the invention provides a system, comprising: a medical facility, comprising: a plurality of locations configured for patient care, each comprising at least one gas fixture, wherein each gas fixture is configured to connect to and supply medical gases to at least one medical device; a medical gas storage facility, comprising a flow meter configured to measure a total gas flow rate from the storage facility; at least one wireless receiver; and a plurality of gas conduits configured to distribute medical gases from the at least one gas storage facility to each of the gas fixtures. In addition, the system further comprises a plurality of wireless sensors disposed on the plurality of gas fixtures, each comprising: a flow sensor configured to measure a flow of gas through the gas fixture on which it is disposed, a connection sensor configured to determine whether a medical device is properly connected to the gas fixture on which it is disposed, and a wireless transmitter configured to transmit a wireless signal to the at least one wireless receiver, wherein the wireless signal includes data indicating whether a flow of gas is detected and whether a medical device is properly connected. In addition, the system further comprises a gas management application, configured to receive the data included in the wireless transmissions, and to selectively generate an alert communicating the existence of a potential leak in the plurality of gas conduits based on the received data.

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein.

DESCRIPTION OF PREFERRED EMBODIMENTS

Figure 1:
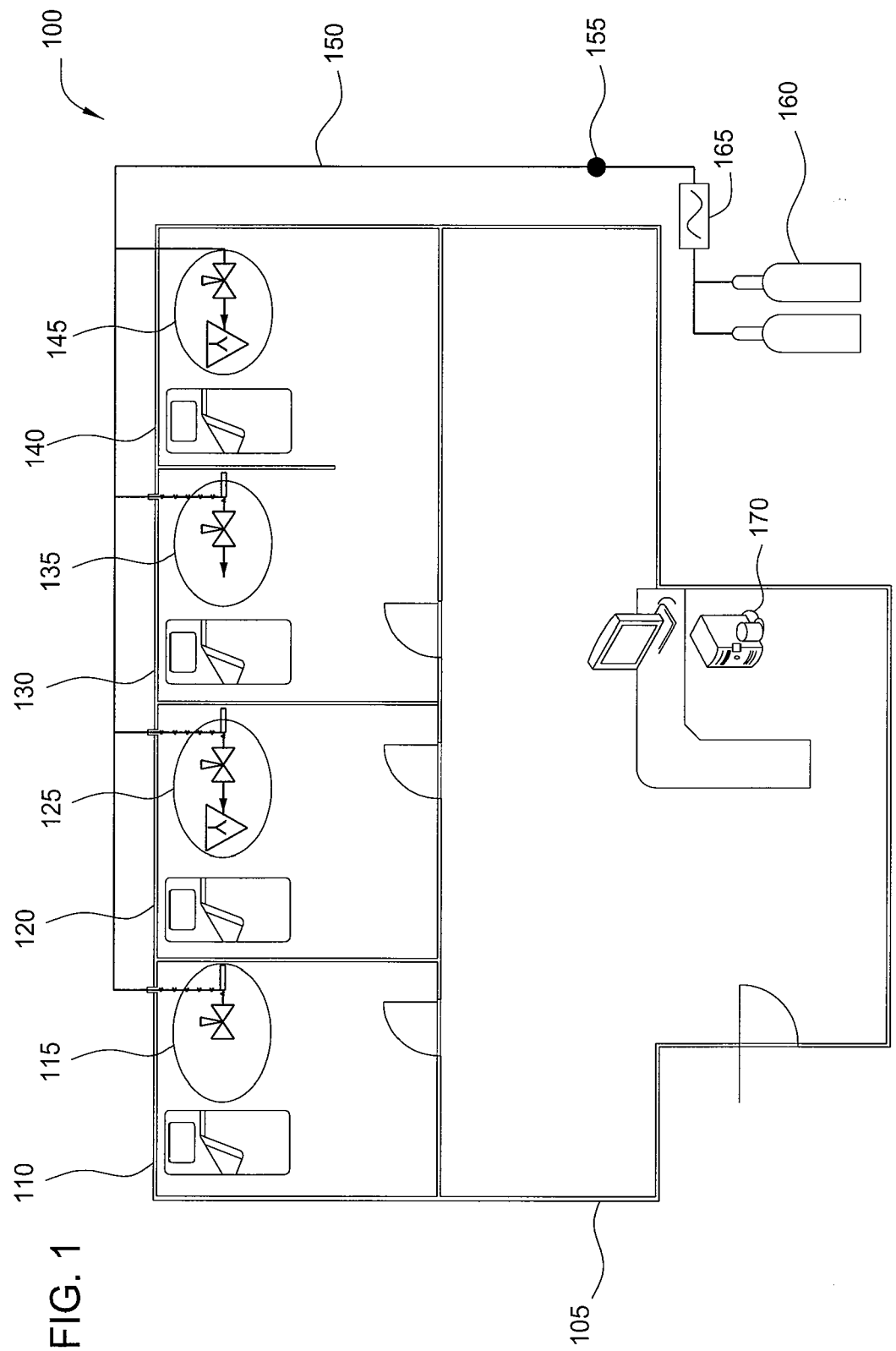
FIG. 1 illustrates an example of a typical medical gas environment.

Embodiments of the present invention generally provide methods and systems for managing a medical gas system by using wireless sensors located at the point of use. In one embodiment, a wireless sensor is fixed to a gas outlet, and is configured to detect any flow of gas, and to detect whether the gas outlet is connected to a medical device. The signal from the wireless device is transmitted to a remote server. If the data carried by the signal (either by itself or in combination with other data) indicates that gas is flowing through the gas outlet, and that no device is connected to the gas outlet, the server generates an alert of a localized leak. In one embodiment, the wireless sensor is configured to transmit the gas flow rate passing through the gas outlet. This data may be used to calculate the total gas used at that point of use. The total gas may then be used to determine when a patient has received a prescribed amount of gas, and/or to calculate a bill for the expense of the gas. In another embodiment, wireless sensors may be fixed to all gas outlets in a medical gas system. By summing the gas flow rate at all gas outlets, and comparing to the gas flow rate measured at a central gas storage facility, it may be determined whether there any leaks in the medical gas system. In another aspect of the invention, the total gas usage for all gas outlets may be compared to a predefined reorder point in order to determine if the gas supply must be replenished.

It is contemplated that any of the foregoing embodiments (and other embodiments disclosed herein) may be done separately or collectively (in any combination) in a given system.

In the following, reference is made to embodiments of the invention. However, it should be understood that the invention is not limited to specific described embodiments. Instead, any combination of the following features and elements, whether related to different embodiments or not, is contemplated to implement and practice the invention. Furthermore, in various embodiments the invention provides numerous advantages over the prior art. However, although embodiments of the invention may achieve advantages over other possible solutions and/or over the prior art, whether or not a particular advantage is achieved by a given embodiment is not limiting of the invention. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

One embodiment of the invention is implemented as a program product for use with a networked computer system such as, for example, the networked system 200 shown in FIG. 2 and described below. The program(s) of the program product defines functions of the embodiments (including the methods described herein) and can be contained on a variety of computer-readable storage media. Illustrative computer-readable storage media include, but are not limited to: (i) non-writable storage media (e.g., read-only memory devices within a computer such as CD-ROM disks readable by a CD-ROM drive) on which information is permanently stored; (ii) writable storage media (e.g., floppy disks within a diskette drive or hard-disk drive) on which alterable information is stored. Such computer-readable storage media, when carrying computer-readable instructions that direct the functions of the present invention, are embodiments of the present invention. Other media include communications media through which information is conveyed to a computer, such as through a computer or telephone network, including wireless communications networks. The latter embodiment specifically includes transmitting information to/from the Internet and other networks. Such communications media, when carrying computer-readable instructions that direct the functions of the present invention, are embodiments of the present invention. Broadly, computer-readable storage media and communications media may be referred to herein as computer-readable media.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-readable format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

Overview of Representative Environment

FIG. 1 illustrates an example of a representative environment 100 of a medical gas system. The environment 100 illustrates aspects of the management of medical gases in the prior art. As shown, the environment 100 includes a medical facility 105, which includes several patient rooms 110, 120, 130, 140, and a server 170. The environment 100 also includes a gas distribution system 150, which distributes medical gases from a gas storage facility 160 to sets of gas fixtures 115, 125, 135, 145 included in the rooms of the medical facility 105. Each set of gas fixtures represents gas equipment that is commonly installed at points of use for gas, for example gas connectors, control valves, and the like. The flow rate of gas to the gas distribution system 150 is measured by a flow meter 165 located near the gas storage facility 160.

As shown, room 110 includes the gas fixtures 115, which are not connected to any medical equipment, and are not releasing any gas (assuming no leaks). Also shown is a room 120, which includes gas fixtures 125 that are providing gas to a connected medical device (e.g., a ventilator). Thus, in the cases of room 110 and room 120, the medical gas system is functioning properly. However, in room 120, determining how much gas has been consumed may require manual readings of any measuring devices included in (or connected to) the gas fixtures 125, according to a conventional approach. Such localized measurements may be required, for instance, to bill a patient for his individual gas usage. Localized measurements may also be required for some medical gases, for example nitric oxide, which are administered to patients in specific amounts as part of therapeutic treatment.

As shown, room 130 includes the gas fixtures 135 which are providing a flow of gas, but which are not connected to any medical devices. Thus, in the case of room 130, there is a gas leak that may only be detected by manual inspection of the gas fixtures 135. In some cases, such leaks may be small, and may thus escape detection by a casual inspection. Such leaks can lead to the waste of medical gases, and thus result in unnecessary cost. Additionally, leaks of some gases (e.g., oxygen) can potentially lead to explosions, while leaks of other gases may lead to toxic conditions.

The room 140 illustrates an example in which a medical device is properly connected to the gas fixtures 145, but is receiving an abnormal flow of gas. This situation may arise, for example, if the controls of the device are not set properly, or if the device malfunctions. Detection of an abnormal gas flow may prevent harm to patients or medical equipment. However, the abnormal gas flow may only be detected on manual inspection of the medical device.

The gas distribution system 150 may include pipes, tubes, conduits, valves, and the like. As illustrated, the gas distribution system 150 may also include a system leak 155. Such leaks may occur at any point in the gas distribution system 150. If the system leak 155 occurs in a location that is usually hidden from view (e.g., inside a wall cavity, in a maintenance duct, etc.), or of the system leak 155 is small, it may be not be noticed, and thus result in an ongoing waste of medical gases. Additionally, such leaks may cause gases to accumulate in hidden locations until they result in explosions or other dangerous conditions.

As described, there are situations which arise in medical gas systems that may result in waste of medical gases. Such situations are costly, and sometimes dangerous. Accordingly, embodiments of the invention provide techniques for detecting these situations. In various embodiments, one or more measuring and communication (i.e., transmitting and/or receiving) devices are fixed to the points of use (e.g., the gas fixtures 115, 125, 135, 145) of a medical facility. In a particular embodiment, one or more of the communication devices are wireless. The communication devices may communicate with a computer system (such as the server 170) configured to make various determinations, including the detecting leaks, monitoring and measuring flow rates, and calculating consumption costs of various gases. Embodiments of the invention are described below.

System Overview

Figure 2:
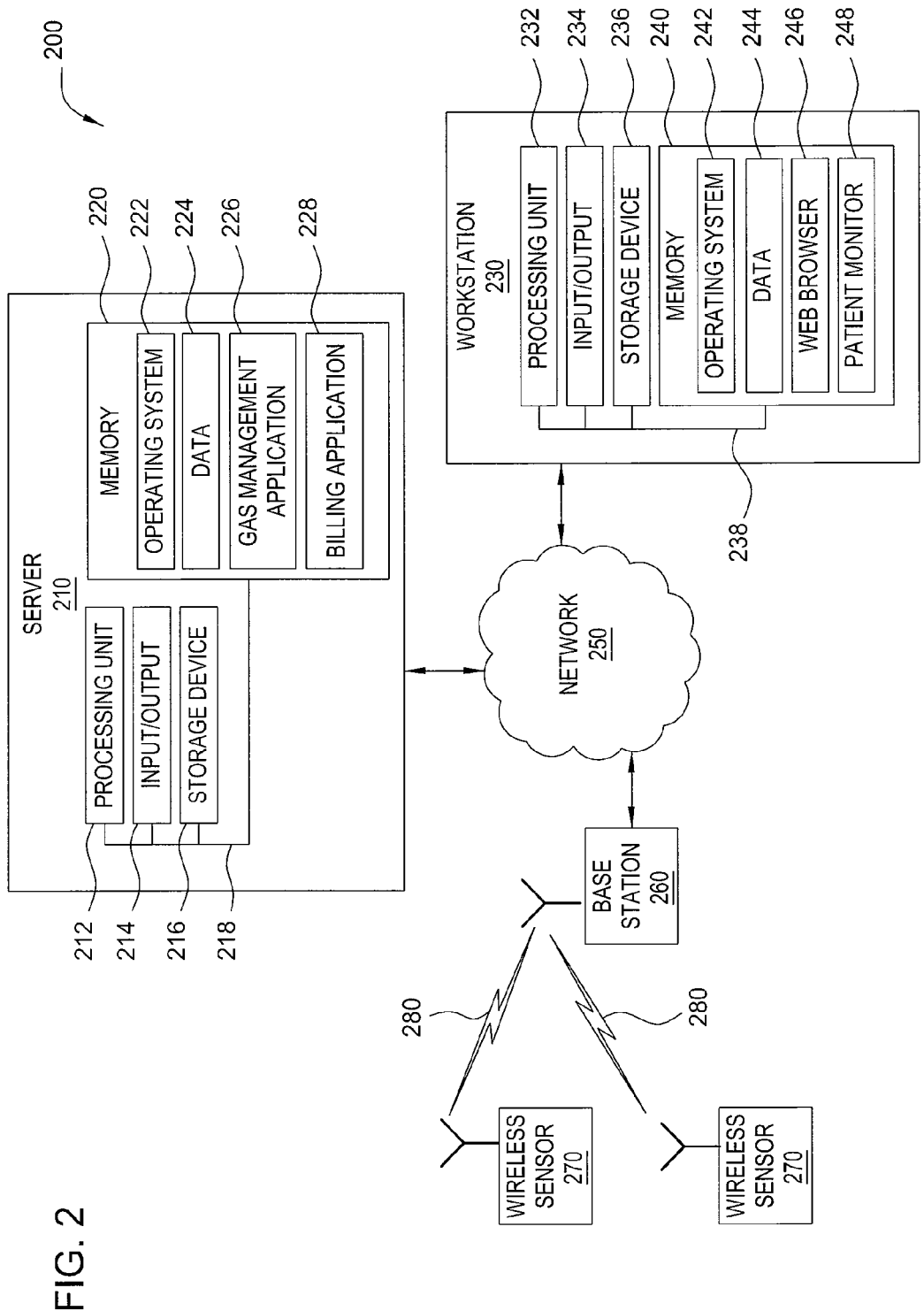
FIG. 2 illustrates a block diagram of a networked system, according to one embodiment of the invention.

Referring now to FIG. 2, a system 200 is shown according to one embodiment of the present invention. In one embodiment of the invention, the system 200 may include a base station 260 configured to receive wireless signals 280 from a set of wireless sensors 270. Each wireless sensor 270 may be configured to detect conditions at a remote portion of a gas delivery system. Such conditions may include the presence of a gas flow, the rate of gas flow, and the proper connection of a device requiring medical gases. The wireless signals 280 may conform to any wireless communication protocols including, for example IEEE 802.11, Global System for Mobile Communications (GSM), Bluetooth, or ZigBee.

In one embodiment, the base station 260 communicates with a central server 210 (which may be the server 170 of FIG. 1). The processing in the central server 210 may be performed by a processing unit 212. The processing unit 212 may process programs in a memory 220, including an operating system 222 for the central database server 210. In addition, the programs may include a gas management application 226 and a billing application 228. The gas management application 226 may be configured to receive and process data from the wireless sensors 270. The gas management application 226 may be further configured to enable the management of a medical gas system by way of a web-based user interface (i.e., Internet web pages). The billing application 228 may be configured to generate patient bills based on, at least in part, the amounts of medical gases consumed in the patient's care. The processing unit 212 may also process data 224 and other programs or information. Such data and programs may also be stored in a storage device 216 such as a hard drive or other computer-readable medium (e.g., a compact disc or read-only memory). The central server 210 may utilize an input/output interface 214 to request and/or receive data from the network 250. Internal components of the central server 210 may communicate via a data bus 218.

A workstation 230 may be used to access the central server 210 over the network 250 and to access the gas management application 226. In one embodiment, processing in the workstation computer 230 may be performed by a processing unit 232. The processing unit 232 may process programs in a memory 240 including an operating system 242 for the workstation computer 230. In addition, the processing unit 232 may also process data 244 and other programs such as a web browser 246 and a patient monitor 248. The web browser 246 may be used to access web applications on the central server 210, such as the gas management application 226. Thus, the web browser 246 may be used to remotely monitor and manage a medical gas system. The patient monitor 248 may be used, for example, to enable a doctor or nurse to monitor the amount of a medical gas administered to a patient as part of a prescribed treatment regimen. Such data and programs may also be stored in a storage device 236 such as a hard drive or other computer-readable medium (e.g., a compact disc or read-only memory). The workstation computer 230 may utilize an input/output interface 234 to request and/or receive data from the network 250. Internal components of the workstation computer 230 may communicate via a data bus 238.

Wireless Sensor

Figure 3:
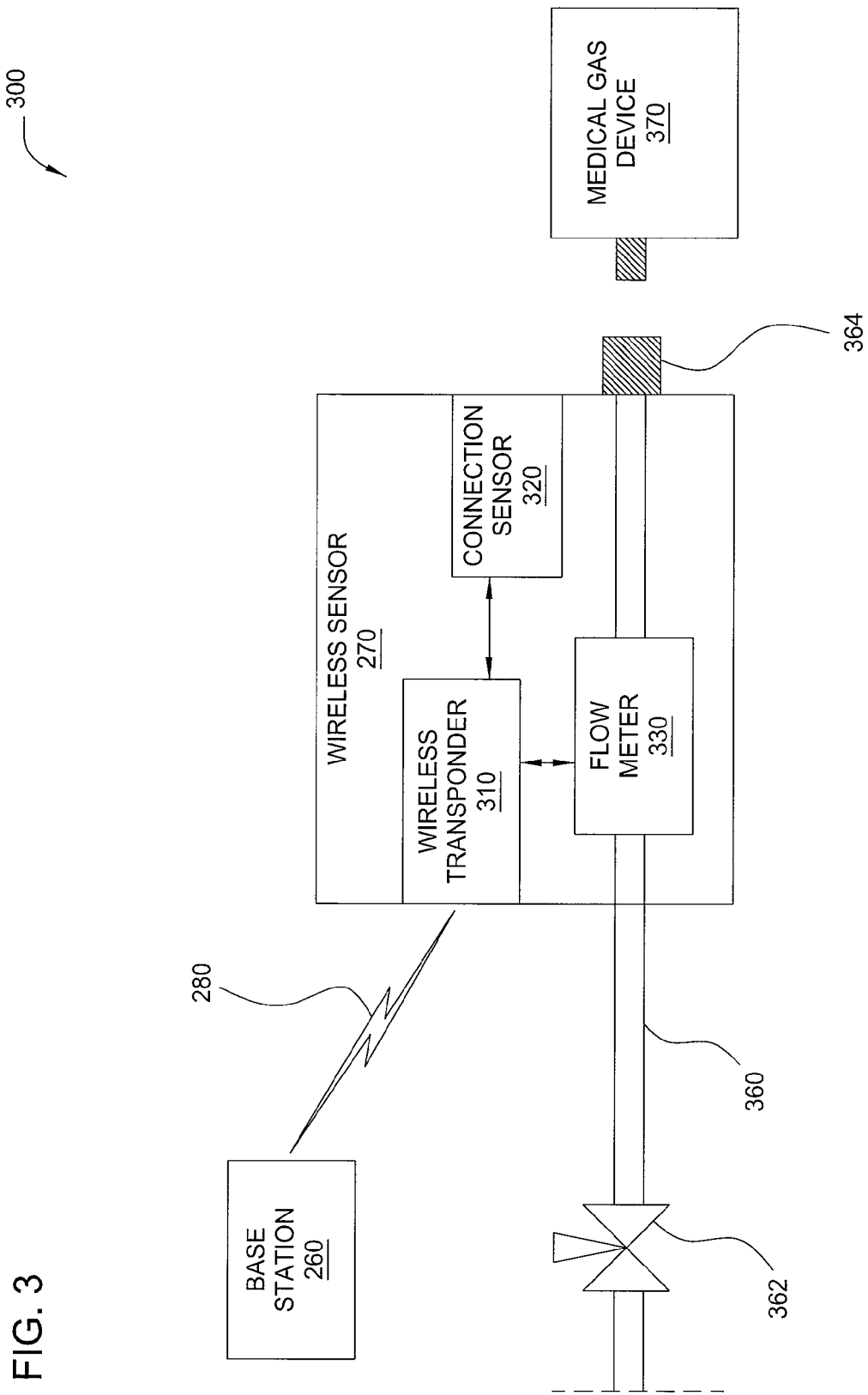
FIG. 3 illustrates a block diagram of a wireless sensor, according to one embodiment of the invention.

FIG. 3 illustrates a block diagram 300 of a wireless sensor 270, according to one embodiment of the invention. As shown, the wireless sensor 270 may be fixed to a gas supply conduit 360, and may be located in proximity to a control valve 362 and a gas connector 364. The control valve 362 may be used to control the supply of gas to a point of use. The gas connector 364 is used to connect a device requiring a supply of a medical gas (e.g., an oxygen ventilator), illustrated in FIG. 3 by a medical gas device 370. In a typical situation, the control valve 362, the wireless sensor 270, and the gas connector 364 may be fixed in a particular point of use of a medical care facility (e.g., as part of gas fixtures 115, 125, 135, 145).

In one embodiment, the wireless sensor 270 may include a connection sensor 320 and a flow meter 330, each connected to a wireless transponder 310. The connection sensor 320 may be configured to detect when a medical gas device 370 is properly connected to the gas connector 364. The connection sensor 320 may operate by any technique known in the art suitable for detecting a proper connection, e.g., electrical contact sensors, pressure switches, optical sensors, magnetic switches, radio-frequency identification (RFID) sensors, and the like.

In one embodiment, the flow meter 330 may be configured to measure the rate of flow of gases passing through a conduit or through the flow meter 330. In another embodiment, the flow meter 330 may instead be configured to detect the presence of a gas flow, without measuring the rate of the flow. In yet another embodiment, the flow meter 330 may be consist of two components, one configured to measure the rate of flow of gases, and another to detect the presence of a gas flow. It is contemplated that the flow meter 330 may be configured in a variety of manners as suited to the intended use.

As shown, the wireless transponder 310 is configured to transmit a wireless signal 280 to a base station 260. The wireless signal 280 may be based on the data generated by the connection sensor 320 and a flow meter 330. That is, the wireless signal 280 may include data describing the flow of gas through the wireless sensor 270 (e.g., the flow rate of gas), and the connection status of the gas connector 364 (e.g., properly connected to a medical device). In one embodiment, the flow rate data generated by the flow meter 330 may be transmitted to the server 210, and then processed by an application for the management of a gas system (e.g., gas management application 226 illustrated in FIG. 2). Further, the flow rate data may be used by to generate a patient bill using, for example, the billing application 228. Furthermore, the flow rate data may be used to monitor a patient's status in undergoing a prescribed treatment with medical gases. This function may be performed using, for example, the patient monitor 248.

In one embodiment, the wireless transponder 310 may be configured to receive wireless signals 280 from the base station 260, with such signals including commands for the operation of the wireless sensor 270 (e.g., to activate the sensor, to run a diagnostic test, etc.). Additionally, the wireless sensor 270 may be configured to control other components of the gas management system. For example, the wireless sensor 270 may be configured to actuate a control valve 362 in response to commands received via wireless signals 280. This action may be performed if a patient has completed a prescribed treatment by receiving a given amount of medical gases.

Of course, the example illustrated in FIG. 3 is provided for illustrative purposes only. It is contemplated that other embodiments may be used to advantage. In one embodiment, the components of wireless sensor 270 may be used as separate components. For example, flow sensor 330 may be located upstream of the control valve x, and the proximity sensor 320 may be fixed to a medical device. Additionally, multiple wireless sensors 270 may be disposed at various points of the gas distribution network 150. By detecting any differences in the flow rates at each point of the gas distribution network 150, any leaks may be isolated to a specific gas supply conduit 360. In another embodiment, the flow sensor 330 and the proximity sensor 320 may each be configured with its own wireless transponder 310. In yet another embodiment, the wireless sensor 270 may be mounted on a mobile medical gas device (e.g., on a portable oxygen unit, or on an anesthesia cart). Any of these embodiments, as well as any other beneficial arrangement of the components of the invention, are included in the scope of the invention.

Flow Diagram of Method

Figure 4:
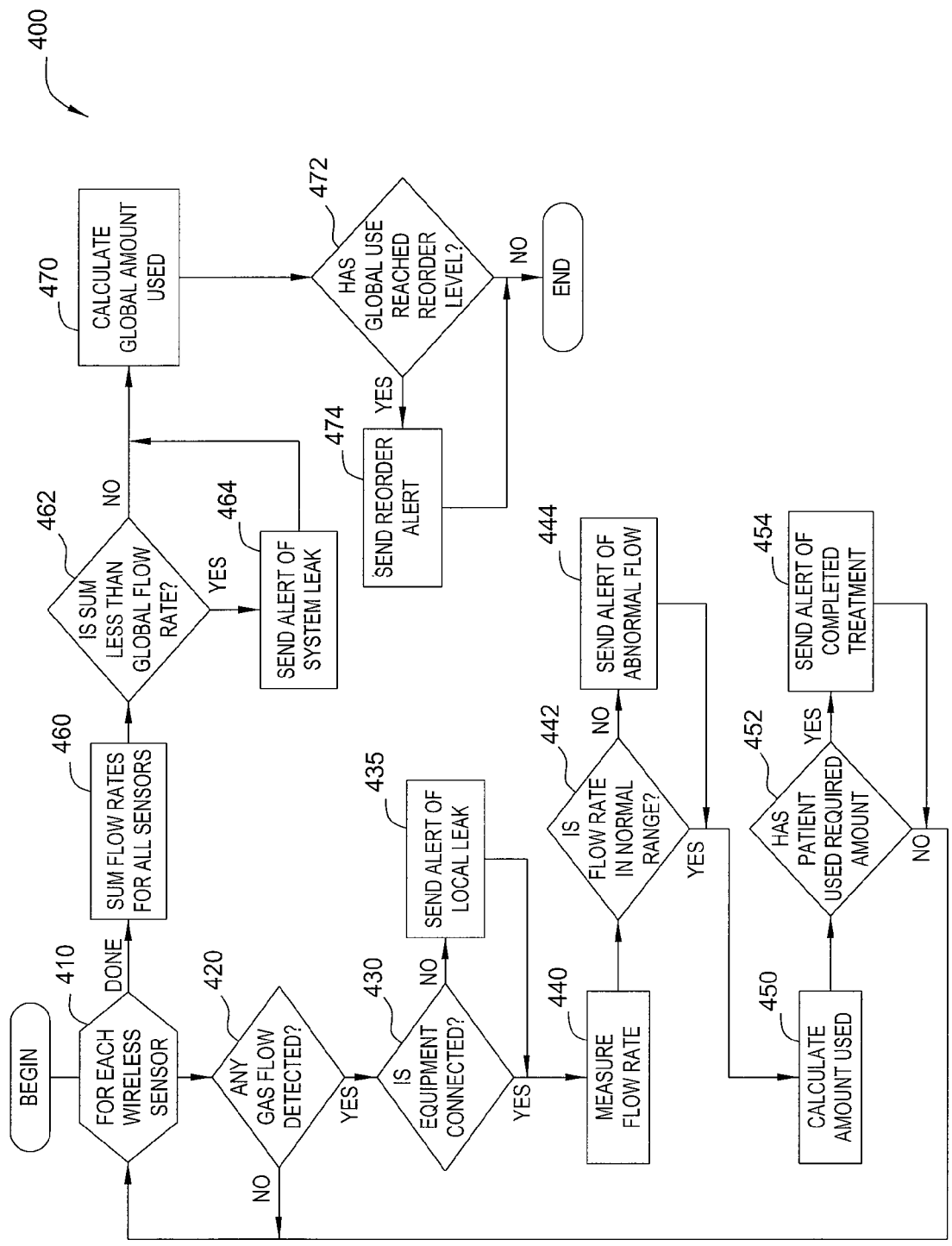
FIG. 4 is a flow diagram depicting a method for the management of medical gases, according to one embodiment of the invention.

FIG. 4 is a flow diagram depicting a method 400 for the management of medical gases, according to one embodiment of the invention. The method 400 begins at step 410, where the method 400 enters a loop (defined by steps 420, 430, 435, 440, 442, 444, 450, 452, and 454) for processing data received from each wireless sensor of multiple wireless sensors included in a medical gas system (e.g., wireless sensor 270 illustrated in FIG. 3). Each wireless sensor may monitor a gas outlet at a point of use of the medical gas system. Some examples of such points of use are illustrated by the gas fixtures 115, 125, 135, and 145 shown in FIG. 1. By processing the data of all wireless sensors, the method 400 may be used to provide an overall view of the entire system, and thus enable the management of the medical gas system.

At step 420, it is determined whether there is any gas flow detected. This step may be based on data collected, for example, by a flow meter 330 included in a wireless sensor 270. If no gas flow is detected (e.g., gas fixtures 115 shown in FIG. 1), the method 400 returns back to step 410 to evaluate the next wireless sensor. Otherwise, the method 400 continues to step 430, where it is determined whether any device is properly connected to the gas outlet (e.g., a medical gas device 370 connected to a gas connector 364). If not, the state exists where a gas flow has been detected (i.e., at step 420), but no device is connected to use the gas flow (e.g., gas fixtures 135 shown in FIG. 1). Thus, at step 435, an alert of a local leak is sent to the central server (e.g., a wireless signal 280 may be sent to the base station 260 connected to a server 210).

The method 400 continues at step 440, where the gas flow rate is measured (e.g., by flow meter 330). Next, at step 442, it is determined whether the measured flow rate is within a predefined range of normal operating flow rates. The predefined range may be based, for example, on the types of medical devices known to be used with the medical gas system. If the measured flow rate is outside the predefined range (e.g., gas fixtures 145 shown in FIG. 1), the method 400 continues to step 444, where an alert of abnormal flow rate is sent to the central server.

The method 400 continues at step 450, where the measured flow rate is used to calculate a total amount of gas used at that particular point of use over a given time period. The calculated amount may be used, for example, for billing a patient for his individual gas usage. Next, at step 452, it is determined whether the calculated amount is equal to (or greater than) a required amount that is prescribed for the patient located at the particular point of use. As is known in the art, a doctor may prescribe a treatment regimen which may include administering a required amount of medical gas to a patient over a period of time. If the patient has received the required amount of gas, the method 400 continues to step 454, where an alert of completed treatment is sent to the central server.

Once the processing of the data from all the wireless sensors of the medical gas system has been completed at step 410, the method 400 continues at step 460, where a sum is calculated of the flow rates measured at step 440. Thus, the calculated sum represents the cumulative total of the gas flows measured at each point of use. Next, at step 462, the calculated sum is compared to a global flow rate, as measured at a central gas storage location (e.g., gas storage facility 160 illustrated in FIG. 1). If the calculated sum is less than the global rate, then the method 400 continues to step 464, where an alert of a system leak is sent to the central server. A system leak may indicate that a hidden leak exists somewhere in the gas distribution network of the medical gas system (e.g., leak 155 shown in FIG. 1). Thus, the system leak alert may be used to, for example, notify maintenance personnel to search for and repair the leak.

The method 400 continues at step 470, where the calculated sum of flow rates is used to calculate a total amount of gas used globally (i.e., for the entire system) over a given time period. Next, at step 472, the global amount of gas used is evaluated to determine if it has reached a predefined reordering level. The reordering level may be set such that, taking into account the current consumption rate and the average time required by suppliers to replenish the gas supply, the new gas supply will arrive shortly before the old gas supply runs out. If the global amount of gas used has not reached the reordering level, the method 400 ends. Otherwise, the method 400 continues to step 474, where a reorder alert may be sent. In addition, step 474 may include sending a replenishment order to the supplier using, for example electronic data interchange (EDI) or web technologies to transmit the order. After step 474, the method 400 ends.

Exemplary Gas Management Application Display

Figure 5:
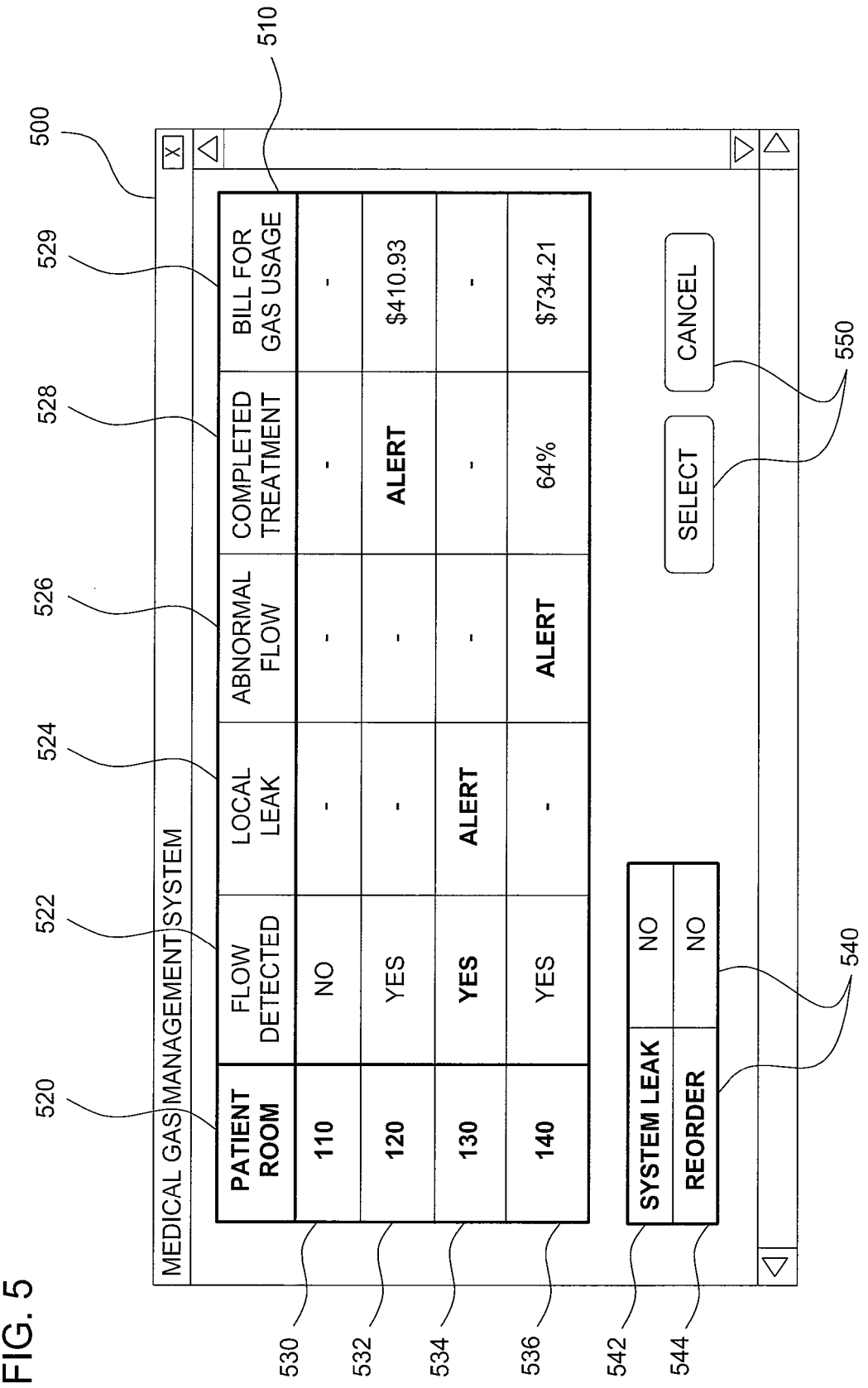
FIG. 5 illustrates a display screen of an application for the management of medical gases, according to one embodiment of the invention.

FIG. 5 illustrates a display screen 500 of an application for the management of medical gases, according to one embodiment of the invention. The display screen 500 may be a graphical user interface (GUI) for the gas management application 226 illustrated in FIG. 2. In one embodiment, the display screen 500 may be viewed by a user at a server (e.g., server 170 shown in FIG. 1 or the server 210 of FIG. 2). Additionally, the display screen 500 may be viewed by user at a workstation (e.g., using web browser 246 on workstation 230 illustrated in FIG. 2).

As shown, the display screen 500 includes a room status summary 510, a system status summary 540, and a set of control buttons 550. The control buttons 550 may enable the user to perform typical functions in the GUI, such as entering data, modifying settings, cancelling commands, etc. The room status summary 510 provides a user with a summary of the status of points of use of a medical gas system. As shown, the room status summary 510 includes a "PATIENT ROOM" column 520, which identifies a particular point of use. In this example, the "PATIENT ROOM" column 520 indicates that the rows 530, 532, 534, 536 correspond to the rooms 110, 120, 130, 140 shown in FIG. 1.

The room status summary 510 also includes a "FLOW DETECTED" column 522, a "LOCAL LEAK" column 524, an "ABNORMAL FLOW" column 526, a "COMPLETED TREATMENT" column 528, and a "BILL FOR GAS USAGE" column 529. These columns generally correspond to the steps of method 400, as described above. In this example, the specific column values correspond to the situations illustrated in FIG. 1. More specifically, the "FLOW DETECTED" column 522 of row 530 indicates that room 110 does not have any detected gas flow. In the case of row 532, the "COMPLETED TREATMENT" column 528 contains the word "ALERT," indicating that the patient in room 120 has completed a treatment regimen of a prescribed amount of a medical gas. This alert may be generated, for example, by the patient monitor 248 shown in FIG. 2. Row 534 includes an alert for the "FLOW DETECTED" column 522, indicating that a gas flow is detected in room 130, but no medical device is properly connected. Row 536 includes an alert in the "ABNORMAL FLOW" column 526, indicating that room 114 is receiving a gas flow outside a predetermined range of operating flow rates. In the case of rooms 120 and 140, the "BILL FOR GAS USAGE" column 529 indicates the current bill for the patient's gas usage.

As shown, the system status summary 540 includes a "SYSTEM LEAK" warning 542. If the sum of the flow rates detected at each room is less than the flow rate measured at a central storage point, there is a possibility of a leak in the gas distribution system (e.g., leak 155). If so, the "SYSTEM LEAK" warning 542 would indicate an alert. The system status summary 540 also includes a "REORDER" warning 544, indicating whether the total gas consumed over a period of time has reached a reordering point.

Preferred processes and apparatus for practicing the present invention have been described. It will be understood and readily apparent to the skilled artisan that many changes and modifications may be made to the above-described embodiments without departing from the spirit and the scope of the present invention. The foregoing is illustrative only and that other embodiments of the integrated processes and apparatus may be employed without departing from the true scope of the invention defined in the following claims.

What is claimed is:

1. A method for monitoring the use of medical gases at the point of use in a wireless medical gas management system, comprising:

providing at least one medical gas source, at least one medical device, at least one medical gas outlet at the point of use that is configured to connect to and supply medical gas from the at least one medical gas source to at least one medical device, a plurality of medical gas conduits configured to distribute the medical gas from the at least one medical gas source to each of the medical gas outlets, and at least one wireless flow sensor fixed to the medical gas conduits, wherein at least one of the wireless flow sensors is in proximity to the each of the medical gas outlets;

receiving, from the wireless flow sensor fixed to the medical gas conduit, a wireless signal indicating the presence of a flow of gas through the medical gas conduit, wherein the medical gas conduit carries gas to the gas outlet;

determining whether the medical device is properly connected to the gas outlet; and if not, generating an alert communicating the existence of a potential leak at the gas outlet.

2. The method of claim 1, wherein determining that a medical device is properly connected to the outlet comprises:

receiving, from a connection sensor fixed to the outlet, a wireless signal indicative of a status of the connection of the medical device to the outlet.

3. The method of claim 1, wherein the wireless signal also indicates a flow rate of gas through the conduit, and further comprising:

determining whether the flow rate of gas is outside a predetermined range of acceptable flow rates; and if so, generating an alert communicating the existence of an abnormal flow rate at the outlet.

4. A computer-readable storage medium storing instructions which when executed by a processor, performs a method, comprising:

receiving, from a flow sensor that is fixed to a medical gas conduit configured to distribute medical gas from at least one medical gas source to at least one medical gas outlet at the point of use a wireless signal indicating the presence of a flow of gas through the conduit, wherein at least one of the wireless flow sensors is in proximity to each of the medical gas outlets, wherein the conduit carries the gas to the gas outlet;

determining whether a medical device is properly connected to the gas outlet; and if not, generating an alert communicating the existence of a potential leak at the gas outlet.

5. The computer-readable storage medium of claim 4, wherein determining that a medical device is properly connected to the outlet comprises:

receiving, from a connection sensor fixed to the outlet, a wireless signal indicative of a status of the connection of the medical device to the outlet.

6. The computer-readable storage medium of claim 4, wherein the wireless signal also indicates a flow rate of gas through the conduit, and further comprising:

determining whether the flow rate of gas is outside a predetermined range of operating flow rates; and if so, generating an alert communicating the existence of an abnormal flow rate at the outlet.

7. The computer-readable storage medium of claim 6, further comprising:

calculating, from the flow rate of gas, a total amount of gas used at the gas outlet over a given period of time.

8. A method for monitoring the use of medical gases at the point of use in a wireless medical gas management system, comprising:

providing at least one medical gas source, at least one ventilator, at least one medical gas outlet at the point of use that is configured to connect to and supply medical gas from the at least one medical gas source to at least one ventilator, a plurality of medical gas conduits configured to distribute the medical gas from the at least one medical gas source to each of the medical gas outlets, and at least one wireless flow sensor fixed to wireless flow sensor fixed to the medical gas conduits, wherein at least one of the wireless flow sensors is in proximity to the each of the medical gas outlets;

receiving, from the wireless flow sensor fixed to the medical gas conduit, a wireless signal indicating the presence of a flow of gas through the medical gas conduit, wherein the medical gas conduit carries gas to the gas outlet;

determining whether the ventilator is properly connected to the gas outlet; and if not, generating an alert communicating the existence of a potential leak at the gas outlet.

* * * * *